United States Patent [19]

Hirosawa et al.

[11] Patent Number: 5,440,032
[45] Date of Patent: Aug. 8, 1995

[54] METHOD FOR PURIFYING ORGANIC SOLUTION CONTAINING LACTAMS

[75] Inventors: Kazuhiko Hirosawa; Yasuhiro Kurokawa; Tomohiko Yamamoto; Masaru Matsunishi; Yoshihiro Nawata, all of Ube, Japan

[73] Assignee: Ube Industries, Ltd., Yamaguchi, Japan

[21] Appl. No.: 712,442

[22] Filed: Jun. 10, 1991

[30] Foreign Application Priority Data

Jun. 12, 1990 [JP] Japan .................. 2-151572

[51] Int. Cl.⁶ ............................................ C07D 201/16
[52] U.S. Cl. .................................. 540/540; 540/464; 540/451; 540/535
[58] Field of Search .................. 540/451, 540, 464, 535

[56] References Cited

U.S. PATENT DOCUMENTS

| | | | |
|---|---|---|---|
| 2,692,878 | 10/1954 | Kahr | 540/540 |
| 2,758,991 | 8/1956 | Kretzers et al. | 540/540 |
| 2,786,052 | 3/1957 | Kampschmidt | 540/540 |
| 2,828,307 | 3/1958 | Soeterbroek et al. | 540/540 |
| 2,883,377 | 4/1959 | Von Schick et al. | 540/464 |
| 3,060,173 | 10/1962 | Von Schick et al. | 540/464 |
| 3,145,198 | 8/1964 | Morbidelli et al. | 540/540 |
| 3,350,392 | 10/1967 | Schultze et al. | 540/464 |
| 3,470,153 | 9/1969 | Schultze et al. | 540/464 |
| 4,120,592 | 10/1979 | Danziger et al. | 540/540 |

*Primary Examiner*—Robert T. Bond
*Attorney, Agent, or Firm*—Finnegan, Henderson Farabow, Garrett & Dunner

[57] ABSTRACT

Disclosed is a method for purifying a lactam-containing organic solution which comprises processing an organic solution containing at least one lactam with an anion exchange resin to remove an anionic surface active substance contained in said organic solution, and then extracting with water to separate an objective component contained in the organic solution to an aqueous solution.

9 Claims, No Drawings

METHOD FOR PURIFYING ORGANIC SOLUTION CONTAINING LACTAMS

BACKGROUND OF THE INVENTION

This invention relates to a method for purifying an organic solution containing lactams. More specifically, it relates to a method for effectively separating and purifying an effective ingredient contained in an organic solution by extracting "an organic solution mainly containing one or more kinds of lactam components" which also contains an anionic surface active substance as an impurity with water.

The method of the present invention can be suitably used when separating $\epsilon$-caprolactam and $\omega$-dodecanelactam by extracting with water "an organic solution containing an anionic surface active substance as an impurity" which is obtained by extracting a mixture of $\epsilon$-caprolactam and $\omega$-dodecanelactam with an organic solvent.

As the method for producing $\epsilon$-caprolactam and $\omega$-dodecanelactam simultaneously, known method is as follows. That is, a mixture of cyclohexanone and cyclododecanone is simultaneously oximated, the resulting mixture containing the produced cyclohexanone oxime or a salt thereof and cyclododecanone oxime or a salt thereof is subjected to Beckmann rearrangement in the presence of sulfuric acid or fuming sulfuric acid. Then, a lactam mixture is obtained by neutralizing the above mixture with ammonia gas or aqueous ammonia, and the lactam mixture is extracted with an organic solvent which is immiscible with water or a lactam oil layer separated from an ammonium sulfate aqueous layer by phase separation of the lactam mixture is extracted with an organic solvent which is immiscible with water to obtain an extract containing lactam components. Further, the extract is reverse extracted with water to transfer $\epsilon$-caprolactam into the aqueous layer whereas $\omega$-dodecanelactam remains in the organic solvent layer (so-called "colactamization method"), which method is described, for example, Japanese Patent Publications No. 7254/1971 and No. 10168/1971).

In the simultaneous preparation method of $\epsilon$-caprolactam and $\omega$-dodecanelactam according to the "colactamization method", the extract containing the above lactam components has heretofore been extracted with water as such. However, in said extracted solution, anionic surface active substances such as alkyl sulfate derived from a straight or branched alkyl alcohol contained in cyclododecanone used as a starting material are present so that, when effecting extraction with water, the organic solvent layer and the aqueous layer are difficult to separate in many cases due to the formation of an emulsion. According to this reason, an extracting tower with a large tower diameter is required. Further, an organic material is contained in the aqueous layer and the aqueous layer becomes turbid whereby causing bad effects on the quality of $\epsilon$-caprolactam, and water-soluble impurities are also contained in the organic solvent layer to cause negative effects on the quality of $\omega$-dodecanelactam.

SUMMARY OF THE INVENTION

An object of the present invention is to provide a method for purifying a lactam-containing organic solution which is suitable for industry in obtaining an effective ingredient with high quality and high yield by preventing formation of an emulsion caused by the above anionic surface active substance and effectively transferring and separating an objective component in an organic solvent layer to an aqueous solution layer when an organic solution containing an anionic surface active substance and at least one lactam is extracted with water.

The present inventors have intensively studied to overcome the various defects in the method of transferring and separating $\epsilon$-caprolactam from an organic solution mainly containing $\epsilon$-caprolactam and $\omega$-dodecanelactam to an aqueous layer by extracting with water as mentioned above, and as a result, they have found that the formation of an emulsion during extraction with water is caused by an "anionic surface active substance" such as alkyl sulfate existing in the above organic solution containing the lactams whereby accomplishing the present invention.

That is, the present invention relates to a method for purifying a lactam-containing organic solution which comprises processing an organic solution containing at least one lactam with an anion-exchange resin to remove an anionic surface active substance contained in said organic solution, and then extracting the processed solution with water to transfer the desired component from the organic solution to the aqueous solution.

As another embodiment of the present invention, the method for purifying a lactam-containing organic solution comprises processing an organic solution containing at least one lactam with a strongly acidic cation exchange resin and then with a weakly basic anion exchange resin to remove an anionic surface active substance contained in said organic solution, and then extracting the processed solution with water to transfer the desired component from the organic solution to the aqueous solution.

DESCRIPTION OF THE PREFERRED EMBODIMENTS

In the following, the method of the present invention will be described in detail.

In the present invention, when transferring and separating at least one of the above effective ingredient (lactams) existing in an organic solution side to an aqueous solution side by extracting with water, the organic solution containing an anionic surface active substance as an impurity, and lactams such as $\epsilon$-caprolactam and $\omega$-dodecanelactam as effective ingredients, and occasionally further containing an organic solvent, the characteristic feature resides in that the above organic solution is processed or treated with an anion exchange resin prior to the above extraction with water whereby the anionic surface active substance as an impurity is removed so that the above extraction with water is carried out effectively.

Further, as the preferred embodiments of the present invention, cyclohexanone and cyclododecanone are simultaneously oximated as a mixture and the resulting mixture containing cyclohexanone oxime or a salt thereof and cyclododecanone oxime or a salt thereof is subjected to Beckmann rearrangement in the presence of sulfuric acid or fuming sulfuric acid, and then the resulting mixture is neutralized with ammonia gas or aqueous ammonia to obtain a lactam mixture mainly containing $\epsilon$-caprolactam, $\omega$-dodecanelactam and ammonium sulfate. Subsequently, the lactam mixture is extracted with an organic solvent which is immiscible with water, or the lactam mixture is allowed to stand to cause phase separation of a lactam oil layer mainly containing ε-caprolactam and ω-dodecanelactam, and an aqueous layer mainly containing ammonium sulfate and the above lactam oil layer is extracted with an organic solvent which is immiscible with water to obtain an extract containing lactam components such as ε-caprolactam and ω-dodecanelactam. Further, the extract is then reverse extracted with water to transfer ε-caprolactam into an aqueous layer, while ω-dodecanelactam remains in the organic solvent layer to separate ε-caprolactam and ω-dodecanelactam. Thereafter, each of the aqueous layer containing ε-caprolactam and the organic solvent layer containing ω-dodecanelactam is purified by using the conventional method such as distillation and others to obtain ε-caprolactam and ω-dodecanelactam simultaneously, which method is called as "colactamization method". In the present invention, by processing with anion exchange resin before reverse extracting the above "lactam mixture or the organic solvent extract of the lactam oil layer" with water, ε-caprolactam which is transferred into an aqueous layer in the subsequently carried out extraction with water can be effectively separated from ω-dodecanelactam which remains in the organic solvent layer.

Also, in the preferred embodiment of the present invention, by processing the "lactam mixture or the organic solvent extract of the lactam oil layer" with strongly acidic cation exchange resin and then with weakly basic anion exchange resin before extracting with water, impurities such as anionic surface active substance can be effectively removed, whereby ε-caprolactam which is transferred into an aqueous layer in the subsequent extraction procedure with water can be effectively separated from ω-dodecanelactam which remains in the organic solvent layer.

In the above lactam mixture or lactam oil layer obtained by Beckmann rearrangement of oximes formed by oximation of cyclohexanone and cyclododecanone and subsequent neutralization, "anionic surface active substance" such as alkyl sulfate as mentioned below is present and it forms an emulsion when transferring and separating ε-caprolactam to the aqueous layer by reverse extracting "the lactam mixture of the organic solvent extract of the lactam oil layer" in the subsequent process whereby separation of ε-caprolactam and ω-dodecanelactam becomes difficult. According to the present invention, however, by processing or treating the above "lactam mixture or the organic solvent extract of the lactam oil layer" with an anion exchange resin prior to extraction with water, the above anionic surface active substance can be removed to the extent that formation of an emulsion no longer occurs.

In the present invention, as the anionic surface active substance contained in the above lactam mixture or the lactam oil layer, there may be mentioned as main substances alkyl sulfuric acid or an alkyl sulfate such as decyl sulfuric acid or a decyl sulfate, undecyl sulfuric acid or a undecyl sulfate, dodecyl sulfuric acid or a dodecyl sulfate, but as others, there may be mentioned amino acid salts such as sodium aminocaproate, aliphatic acid salts, alkylsulfonates and alkylarylsulfonates. As the alkylsulfates, ammonium salt thereof is particularly mentioned.

These anionic surface active substances are caused by a straight alkyl alcohol or branched alkyl alcohol such as n-decyl alcohol, n-undecyl alcohol and n-dodecyl alcohol, contained in the starting materials, cyclohexanone and cyclododecanone, particularly in cyclododecanone. When preparing the above lactam mixture mainly containing ε-caprolactam and ω-dodecanelactam from cyclohexanone and cyclododecanone through oximation process, transformation process and neutralization process, these straight or branched alkyl alcohols react with sulfuric acid or fuming sulfuric acid to form the above alkyl sulfuric acid (or alkyl sulfate).

In the anionic surface active substances contained in the above lactam mixture, alkyl sulfuric acid or alkyl sulfate is particularly contained in large amounts, for example, a content of decyl sulfuric acid (or decyl sulfate) and undecyl sulfuric acid (or undecyl sulfate) is about 30 to 500 ppm by weight, and that of dodecyl sulfuric acid (dodecyl sulfate) is about 50 to 1000 ppm by weight.

In the present invention, a content of ε-caprolactam or ω-dodecanelactam in an extract solution obtained by extracting the lactam mixture mainly containing ε-caprolactam, ω-dodecanelactam and ammonium sulfate, or the lactam oily layer mainly containing ε-caprolactam and ω-dodecanelactam, which is separated by phase separation of the lactam mixture from the ammonium sulfate aqueous layer, with an organic solvent immiscible with water is preferably 10 to 20 % by weight, respectively.

Also, as the organic solvent to be used in the present invention, there may be mentioned a solvent which is liquid at an extraction temperature and immiscible with water such as aromatic hydrocarbons including benzene, toluene, xylene and isopropylbenzene; alicyclic hydrocarbons including cyclohexane and cyclooctane; aliphatic hydrocarbons having 6 to 8 carbon atoms including n-hexane, n-heptane and n-octane; and hydrocarbons substituted by a halogen atom(s) including trichloroethylene, carbon tetrachloride and chloroform. Among these, benzene and toluene are most suitable. Of course, it is needless to say that two or more kinds of the above solvents may be used in combination.

Next, processing (treatment) with an anion exchange resin of "the organic solution (lactam-containing organic solution) containing lactam components such as ε-caprolactam and ω-dodecanelactam as effective ingredients" such as the above "lactam mixture or the organic solvent extract of the lactam oil layer" which is the characteristic feature of the present invention will be mentioned.

In the present invention, either one of the conventionally known four types of anion exchange resins having a primary amino group, secondary amino group, tertiary amino group or quaternary ammonium group ($-N^+(CH_3)_3 \cdot X^-$ where $X^-$ is an anion) as an exchange group may be used. But particularly preferably used is a strongly basic anion exchange resin having a quaternary ammonium salt group as an ion exchange group. As a gel type anion exchange resin, there may be mentioned, for example, Amberlite IRA-420 (trade name, available from ROHM & HAAS Co.), and as a macroreticular type anion exchange resin, there may be mentioned, for example, Amberlite IRA-900 (trade name, available from ROHM & HAAS Co.) and Amberlex-600 (trade name, available from ORGANO Co.).

As the strongly acidic cation exchange resin, those having a sulfonyl group ($-SO_3M$ where M is an atom or a group which can form a salt with sulfonyl group) can be used. As an example of a macroreticular type strongly acidic cation exchange resin, there may be mentioned, for example, Amberlite 200 (trade name, available from ROHM & HAAS Co.).

As the weakly basic anion exchange resin, those having a tertiary amine functionality ($-N(CH_3)_2$) can be used. As a gel type weakly basic anion exchange resin, there may be mentioned, for example, Amberlite IRA-68 (trade name, available from ROHM & HAAS Co.), and as a macroreticular type weakly basic anion exchange resin, there may be mentioned, for example, Amberlite IRA-35 (trade name, available from ROHM & HAAS Co.).

In the present invention, alkyl sulfates have a large molecular size so that macroreticular type ion exchange resins having macro-network structure are more preferred than the gel type ones having a smaller pore size since the resin can be easily regenerated.

In the method of purifying the lactam-containing solution with the strongly basic anion exchange resin, alkyl sulfates can be adsorbed and removed even when they are in the form of a salt and installation cost can be made small. Also, in the method of purifying the same with the strongly acidic cation exchange resin and then with the weakly basic anion exchange resin, regeneration of the resin is extremely easy since adsorbing power to alkyl sulfate is weak.

The above lactam-containing organic solution may be processed with the above anion exchange resin as such or without pre-treatment, but in order to effect adsorption and separation due to the above anion exchange resin effectively, it is preferred to process with the above anion exchange resin after addition of water to the above lactam-containing organic solution with an amount of an equivalent amount or less, preferably 5 % by weight or less, more preferably 1 to 2 % by weight based thereon.

The method for adding water to the above lactam-containing organic solution is not particularly limited, but when the processing with the above anion exchange resin with the "fixed bed system" as mentioned below, it is preferred, for example, to add a predetermined amount of water to the lactam-containing organic solution immediately before the anion exchange resin processing. Also, when the processing with the above anion exchange resin is carried out by the "suspension system", it is preferred, for example, to process the lactam-containing organic solution by charging the above lactam-containing organic solution in a tank type vessel equipped with a stirrer, then adding water thereto with a ratio as mentioned above, and suspending the above anion exchange resin in the mixed solution of the above lactam-containing organic solution and water.

If the added amount of water to the above lactam-containing organic solution exceeds an equivalent amount as mentioned above, it is not preferred since much energy is required when condensing and purifying an $\epsilon$-caprolactam aqueous solution in order to recovering $\epsilon$-caprolactam from the $\epsilon$-caprolactam aqueous solution obtained by extraction with water of the above lactam-containing organic solution, or crystals of $\omega$-dodecanelactam are precipitated from the mixture of the above lactam-containing organic solution and water.

Also, a processing amount of the above lactam-containing organic solution or the mixed solution thereof and water is desirably 20 $m^3/hr\cdot m^3$-Resin or less, particularly preferably 6 $m^3/hr\cdot m^3$-Resin or less represented by a "load flow rate against the anion exchange resin.

A processing temperature of the above lactam-containing organic solution or a mixed solution thereof and water may be the boiling temperature of the organic solution or the mixture or less and 80° C. or less, particularly preferably 40° to 70° C. When processing the above lactam-containing organic solution or a mixed solution thereof and water with the anion exchange resin, the method for maintaining the temperature of the above lactam-containing organic solution or a mixed solution thereof and water within the above range is not particularly limited. However, there may be considered, for example, the method in which the lactam-containing organic solution or the anion exchange resin in the processing tank is heated by passing hot water through a jacket portion of the processing tank equipped with a jacket.

In the present invention, as the processing method with the anion exchange resin, either of "the fixed bed system" in which, for example, the above lactam-containing organic solution or the mixed solution thereof and water is passed through a resin tower filled with the anion exchange resin, or "the suspension system" in which, for example, the anion exchange resin is suspended in the above lactam-containing organic solution or the mixed solution thereof and water charged in a tank type vessel equipped with a stirrer may be applied to, but "the fixed bed system" is more preferred since regenerating operations of the anion exchange resin are easier.

As the regenerating processing system of the anion exchange resin adsorbed the above anionic surface active substances in the above lactam-containing organic solution, there may be mentioned (a) the method in which after passing a sulfuric acid aqueous solution, regenerating with caustic soda (sodium hydroxide) aqueous solution, (b) the method of regenerating with a brine, (c) the method of regenerating only with caustic soda aqueous solution, and (d) the method of regenerating with a brine and a caustic soda aqueous solution. Among these, the most preferred method is the method of regenerating with a brine and a caustic soda, and when the regenerating processing with a brine and a caustic soda is carried out, the above anion exchange resin can recover substantially the same processing ability as that of the initial one. In this case, a concentration of the sulfuric acid aqueous solution, the caustic soda aqueous solution or the brine is preferably 1 to 10 % by weight or so, respectively.

In this invention, the degree of removing the anionic surface active substances in the above lactam-containing organic solution with the anion exchange resin may vary depending on the content of the anionic surface active substances in the above lactam-containing organic solution or the conditions of the extracting operation during the subsequent water-extraction process so that it cannot be defined. In the present invention, however, it may be the extent that an emulsion is not formed by the anionic surface active substances in the above lactam-containing organic solution or the mixed solution thereof and water supplied to the water-extraction process. Accordingly, the above processing conditions due to the anion exchange resin may be determined by referring to the content of the anionic surface active substances in the above lactam-containing organic solution, or the conditions of the extracting operation employed in the subsequent water-extraction process.

The lactam-containing organic solution or the mixed solution thereof and water in which the anionic surface active substances are removed is then applied to the extraction procedure with water. Conditions of the extracting operation or extracting method such as an extraction temperature, a ratio of the extracting agent, an extraction time, the time allowed to stand for separation of the solutions after extraction, model of the extracting device are not particularly limited, and it may be the method applied to the conventional liquid-liquid extraction.

The method of preventing formation of an emulsion during extraction with water which is subsequently carried out after processing the lactam-containing organic solution with the anion exchange resin to remove the anionic surface active substance contained in said lactam-containing organic solution is described above. As the method of preventing formation of emulsion during extraction of the above lactam-containing organic solution with water, it is not restricted only to "the method of processing with an anion exchange resin", but may be the method in which a cationic surfactant is added to "the lactam-containing organic solution" containing the anionic surface active substances.

Further, the method of the present invention can be also applied to the case where impurities which cause formation of an emulsion are contained in the above organic solution in which at least one of the desired components in the organic solution is transferred to the aqueous layer and separated according to the water extraction, in the processes of separating $\epsilon$-caprolactam transferred into the aqueous layer by extracting the above lactam-containing organic solution with water and $\omega$-dodecanelactam remains in the organic layer, and then purifying the $\epsilon$-caprolactam and $\omega$-dodecanelactam, respectively.

Furthermore, according to the method of the present invention, it is needless to say that, in the method of transferring and separating at least one of the objective components contained in the organic solution containing the cationic surface active substance to the aqueous layer by extracting with water, formation of an emulsion at the above extraction with water can be prevented and transferring and separation of at least one of the above objective components to the aqueous layer side can be effectively carried out by processing the organic solution containing a cationic surface active substance with a cation exchange resin or adding an anionic surfactant to the organic solution containing the cationic surface active substance.

EXAMPLES

Next, the method of the present invention will be explained in more detail by referring to Examples and Comparative examples, but the present invention is not limited to the following Examples so long as not exceeding the purposes thereof.

EXAMPLE 1

To a toluene solution containing 14% by weight of $\epsilon$-caprolactam and 11% by weight of $\omega$-dodecanelactam as lactam components and 150 ppm of alkyl sulfate in terms of ammonium dodecylsulfate was added 2% by weight of water based on the toluene solution, and the resulting mixed solution was continuously fed to a glass column filled with 60 ml of a strongly basic anion exchange resin (trade name: Amberlex 600, available from ORGANO CO.) at a temperature of 60° C. and at a feed rate of 360 ml/hr for 13 hours.

The resulting toluene solution obtained by the processing with the anion exchange resin was stored in a vessel and collected by every one hour, and it was extracted with water under the following conditions. That is, 320 g of the toluene solution (processed solution) processed with the anion exchange resin were charged in a vessel having a volume of 2 liter and made of a glass equipped with a stirrer, then 460 g of water was added thereto, and the mixture was stirred to effect extraction with water by the batch operation. As the results, in either of the extraction with water of the processing solutions, an organic layer (toluene layer) and an aqueous layer were easily separated within a short time by allowing to stand, whereby 274 g of a toluene solution of $\omega$-dodecanelactam and 506 g of a toluene solution of $\epsilon$-caprolactam both of high transparency can be obtained.

Compositions of the toluene phase and the aqueous phase after extraction with water of the processed solution obtained during 4 to 5 hours after initiation of supply of the above toluene solution to the above glass column measured by gas chromatography are as follows. In either of the extraction with water of the processing solution, substantially the same results can be obtained.

|  | Toluene phase | Aqueous phase |
|---|---|---|
| $\epsilon$-caprolactam | 2.8 wt % | 7.1 wt % |
| $\omega$-dodecanelactam | 12.0 wt % | 0.08 wt % |

COMPARATIVE EXAMPLE 1

In a vessel made of glass having a volume of 2 liter and equipped with a stirrer were charged 320 g of the toluene solution having the same composition as in Example 1 and 460 g of water, and stirring was continued for 15 minutes to effect extraction with water.

When stopping the stirring and the mixture was allowed to stand, emulsion was formed in the whole vessel to cause difficulty in separation between the toluene phase and the aqueous phase.

At after 30 minutes from stopping the stirring, whereas the toluene phase and the aqueous phase were separated, an emulsion intermediate layer remained at the surface therebetween, and the aqueous phase containing $\epsilon$-caprolactam was turbid.

EXAMPLE 2

To a benzene solution containing 13% by weight of $\epsilon$-caprolactam and 13% by weight of $\omega$-dodecanelactam as lactam components and 150 ppm of alkyl sulfate in terms of ammonium dodecylsulfate was added 2% by weight of water based on the benzene solution, and the resulting mixed solution was continuously fed to a glass column filled with 60 ml of a strongly basic anion exchange resin (trade name: Amberlite IRA-420, available from ORGANO CO.) at a temperature of 60° C. and at a feed rate of 180 ml/hr for 30 hours.

The resulting benzene solution (processed solution) obtained by the processing with the anion exchange resin was stored in a vessel and collected by every two hours, and it was extracted with water under the same conditions as in Example 1 to obtain 280 g of an organic phase (benzene phase) and 500 g of an aqueous phase both having high transparency without forming emulsion and with easy phase separation.

Compositions of the benzene phase and the aqueous phase after extraction with water of the processed solution obtained during 16 to 18 hours after initiation of supply of the above benzene solution to the above glass column are as follows. In either of the extraction with water of the processing solution, substantially the same results can be obtained.

|                  | Benzene phase | Aqueous phase |
|------------------|---------------|---------------|
| ε-caprolactam    | 2.6 wt %      | 6.7 wt %      |
| ω-dodecanelactam | 14.0 wt %     | 0.09 wt %     |

COMPARATIVE EXAMPLE 2

In a vessel made of glass having a volume of 2 liter and equipped with a stirrer were charged 320 g of the benzene solution having the same composition as in Example 2 and 460 g of water, and stirring was continued for 15 minutes to effect extraction with water.

When stopping the stirring and the mixture was allowed to stand, emulsion was formed in the whole vessel to cause difficulty in separation between the benzene phase and the aqueous phase.

At after 30 minutes from stopping the stirring, whereas the benzene phase and the aqueous phase were separated, an emulsion intermediate layer remained at the surface therebetween, and the aqueous phase containing ε-caprolactam was turbid.

In the "colactamization method" which produces ε-caprolactam and ω-dodecanelactam simultaneously, a lactam mixture obtained by subjecting cyclohexanone and cyclododecanone to oximation procedure, Beckmann rearrangement procedure and further neutralization procedure is extracted with an organic solvent immiscible with water, then the resulting lactam-containing organic solution is extracted with water to transfer and separate ε-caprolactam in the lactam-containing organic solution to an aqueous layer whereby ε-caprolactam and ω-dodecanelactam are separated and purified. However, in the above lactam-containing organic solution, an anionic surface active substance is present as an impurity so that it causes the problems that difficulty in separation between the organic solvent layer and the aqueous layer accompanied by formation of emulsion is likely caused in the extraction procedure with water, whereby an extraction tower with a larger tower size is required. Further, an organic material is accompanied by an aqueous layer to cause turbidity and bad effects to the quality of ε-caprolactam or water-soluble impurities are accompanied by the organic solvent layer and they have a bad effect on the quality of ω-dodecanelactam. To the contrary, according to the method of the present invention, as mentioned above, it can be accomplished the effect of providing a purifying method of the lactam-containing organic solution which can prevent formation of an emulsion in the extraction procedure with water whereby (a) migration of an organic layer containing a high amount of impurities into an aqueous layer can be prevented and ε-caprolactam with high quality can be obtained, (b) migration of an aqueous layer containing water-soluble impurities can be prevented and ω-dodecanelactam with high quality can be obtained, and also (c) lowering in extraction efficiency at the extraction procedure with water can be prevented so that ε-caprolactam and ω-dodecanelactam can be recovered with high yield, and further (d) when effecting the extraction with water by continuous counter-current extraction, processing can be carried out with a tower having small tower size.

According to the above, an extraction tower with high theoretical number of steps can be applied to so that improvement in the extraction efficiency can be expected from a device and also complicated extracting operations accompanied by enlargement of the device can be resolved.

We claim:

1. A method for purifying a lactam-containing organic solution which comprises:
   (a) obtaining an organic solution containing ε-caprolactam and ω-dodecanelactam by the colactamization method comprising
      i) oximating simultaneously a mixture of cyclohexanone and cyclododecanone,
      ii) subjecting the resulting mixture from (i) of cyclohexanone oxime or a salt thereof and cyclododecanone oxime or a salt thereof to Beckmann rearrangement in the presence of sulfuric acid or fuming sulfuric acid,
      iii) neutralizing the resulting mixture of (ii) with ammonia gas or aqueous ammonia to obtain a lactam mixture mainly containing ε-caprolactam, α-dodecanelactam, and ammonium sulfate, and
      iv) extracting the lactam mixture of (iii) or an oily layer obtained by allowing the lactam mixture of (iii) to stand and separate into an oily layer and an aqueous layer, with an organic solvent to obtain an organic solution containing ε-caprolactam, ω-dodecanelactam and an anionic surface active substance,
   (b) processing the organic solution of (a)(iv) with an anion exchange resin in the presence of 5% by weight or less of water based on the weight of said organic solution to remove the anionic surface active substance contained in said organic solution, and then
   (c) extracting the product of (b) with water to separate ε-caprolactam contained in the organic solution into an aqueous solution.

2. The method according to claim 1, wherein said anion exchange resin is a strongly basic anion exchange resin having a quaternary ammonium salt group.

3. The method according to claim 2, wherein said anion exchange resin is Amberlex 600 (trade name) or Amberlite IRA-420 (trade name).

4. The method according to claim 1, wherein anionic surface active substances contained in said organic solution are alkyl sulfuric acids, alkyl sulfates, amino acid salts, aliphatic acid salts, alkylsulfonates or alkylarylsulfonates.

5. The method according to claim 4, wherein said alkyl sulfuric acid or an alkyl sulfate is decyl sulfuric acid, decyl sulfate, undecyl sulfuric acid, undecyl sulfate, dodecyl sulfuric acid or dodecyl sulfate.

6. The method according to claim 1, wherein before the processing with an anion exchange resin, processing with a strongly acidic cation exchange resin is carried out.

7. The method according to claim 6, wherein said anion exchange resin is a weakly basic anion exchange resin.

8. The method according to claim 7, wherein said weakly basic anion exchange resin is Amberlite IRA-68 (trade name) or Amberlite IRA-35 (trade name).

9. The method according to claim 6, wherein said strongly acidic cation exchange resin is Amberlite 200 (trade name).

* * * * *

UNITED STATES PATENT AND TRADEMARK OFFICE
CERTIFICATE OF CORRECTION

PATENT NO. : 5,440,032
DATED : August 08, 1995
INVENTOR(S) : Kazuhiko HIROSAWA et al It is certified that error appears in the above-indentified patent and that said Letters Patent is hereby corrected as shown below:

Claim 1, column 10, line 23, "$\alpha$" should read --$\omega$--.

Signed and Sealed this

Twentieth Day of August, 1996

Attest:

BRUCE LEHMAN

*Attesting Officer*     *Commissioner of Patents and Trademarks*